United States Patent [19]
Zhu et al.

[11] Patent Number: 5,293,863
[45] Date of Patent: Mar. 15, 1994

[54] BLADED ENDOSCOPIC RETRACTOR

[75] Inventors: Yong H. Zhu, Loma Linda; Wolff M. Kirsch, Redlands, both of Calif.

[73] Assignee: Loma Linda University Medical Center, Loma Linda, Calif.

[21] Appl. No.: 880,757

[22] Filed: May 8, 1992

[51] Int. Cl.⁵ .......................................... A61B 17/02
[52] U.S. Cl. .................................... 128/20; 606/198
[58] Field of Search ............... 128/17, 20, 4, 751; 606/198, 191, 205, 206, 207; 604/104, 105, 106, 107, 108, 109

[56] References Cited

U.S. PATENT DOCUMENTS

| | | |
|---|---|---|
| 3,044,461 | 7/1962 | Murdock . |
| 3,312,222 | 4/1967 | Dwyer . |
| 3,316,912 | 5/1967 | Whitaker ........................ 606/191 X |
| 4,178,920 | 12/1979 | Cawood, Jr. et al. ................... 128/4 |
| 4,654,028 | 3/1987 | Suma . |
| 4,692,139 | 9/1987 | Stiles . |
| 4,744,363 | 5/1988 | Hasson . |
| 4,763,669 | 8/1988 | Jaeger .................................. 128/751 |
| 4,872,456 | 10/1989 | Hasson ................................. 606/207 |
| 4,880,015 | 11/1989 | Nierman .............................. 128/751 |
| 4,909,789 | 3/1990 | Taguchi et al. . |
| 4,921,485 | 5/1990 | Griffiths . |
| 5,002,543 | 3/1991 | Bradshaw et al. ................ 606/95 X |
| 5,052,402 | 10/1991 | Bencini et al. ................. 606/206 X |
| 5,152,279 | 10/1992 | Wilk ....................................... 128/17 |
| 5,195,506 | 3/1993 | Hulfish ................................ 128/4 X |

FOREIGN PATENT DOCUMENTS 0449663 10/1991 European Pat. Off. .
8911827 12/1989 PCT Int'l Appl. .
9307816 4/1993 PCT Int'l Appl. .

Primary Examiner—Richard J. Apley
Assistant Examiner—Karen A. Jalbert
Attorney, Agent, or Firm—Knobbe Martens Olson & Bear

[57] ABSTRACT

A retractor is provided for use during endoscopic surgery. Bladed instruments located inside the patient's body at an insertion end of the retractor are manipulated by controls located outside the body at a control end. In three embodiments, the retractor comprises a tubular body having an insertion and control end. Two blades are movably connected in the insertion end of the body. The blades may be moved in various combinations, being extended away from the longitudinal axis of the retractor body and/or spread apart. The blades may be actuated with controls which extend from the control end of the body. In another embodiment, the retractor comprises a tubular body also having an insertion and control end. Three blades are movably attached to the insertion end of the body. The blades may be independently extended radially outward from the longitudinal axis of the retractor body. Each blade is actuable from a separate control located at the control end of the body.

30 Claims, 9 Drawing Sheets

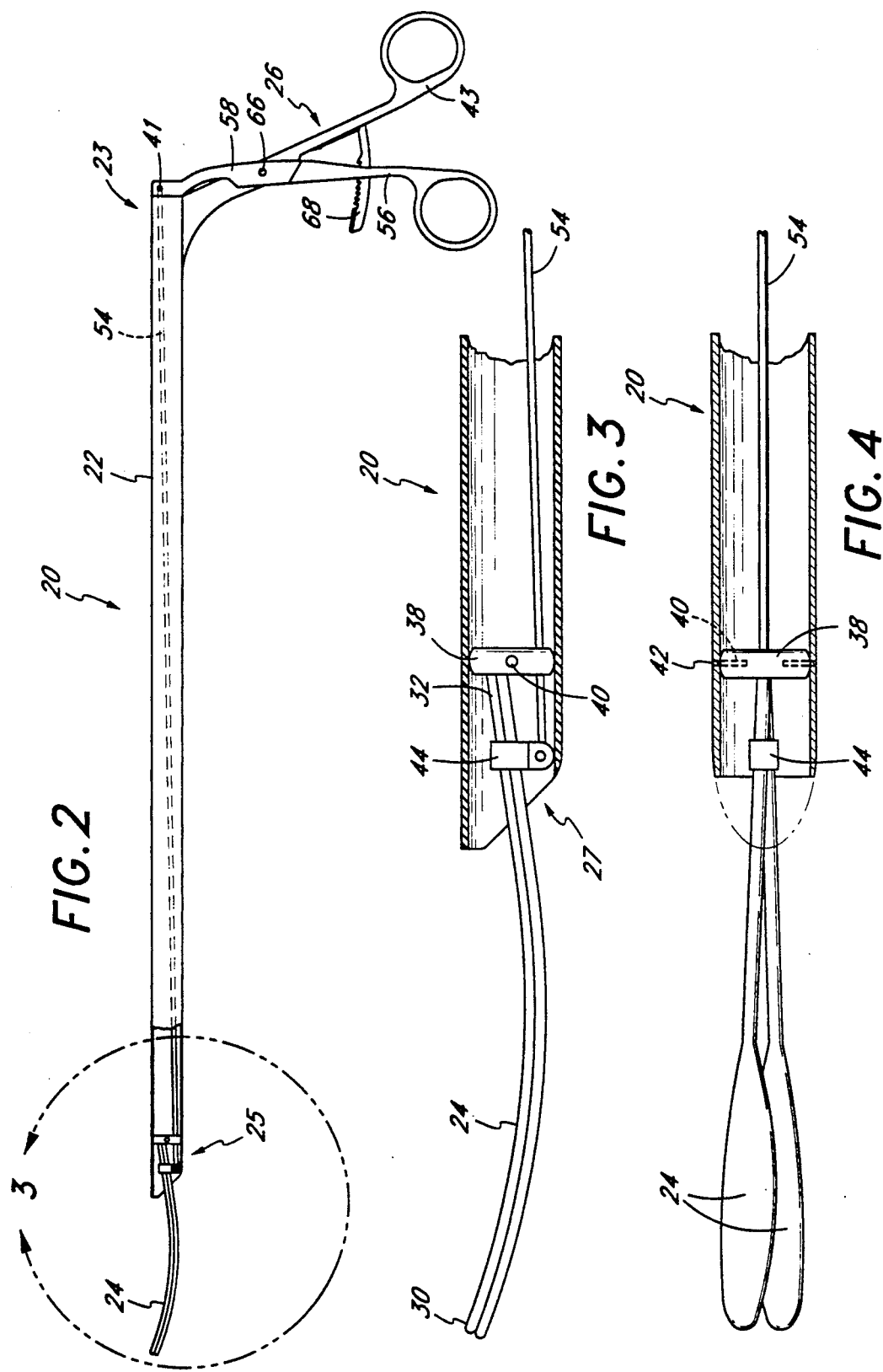

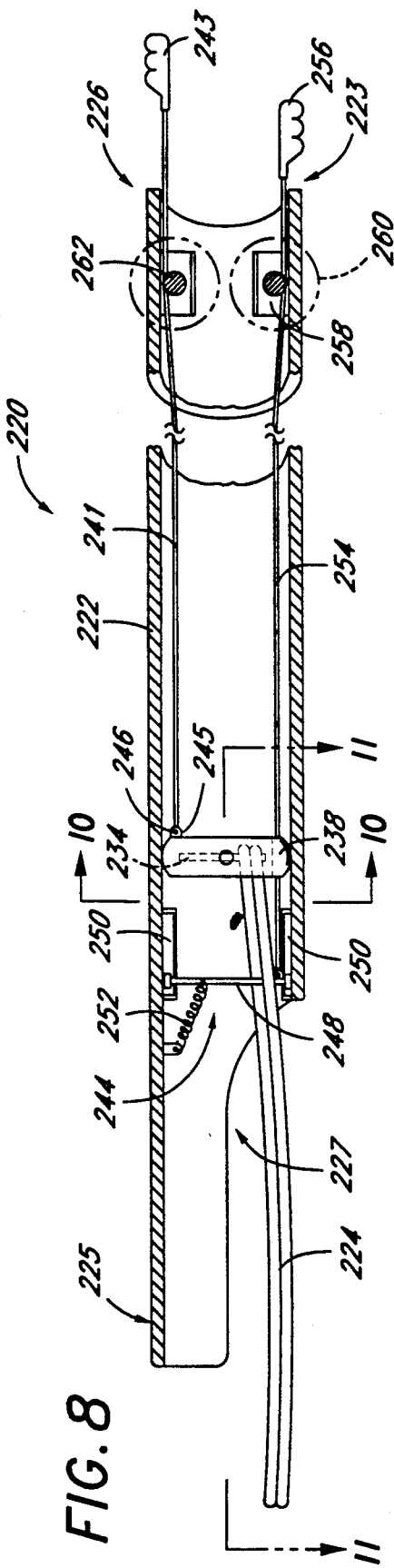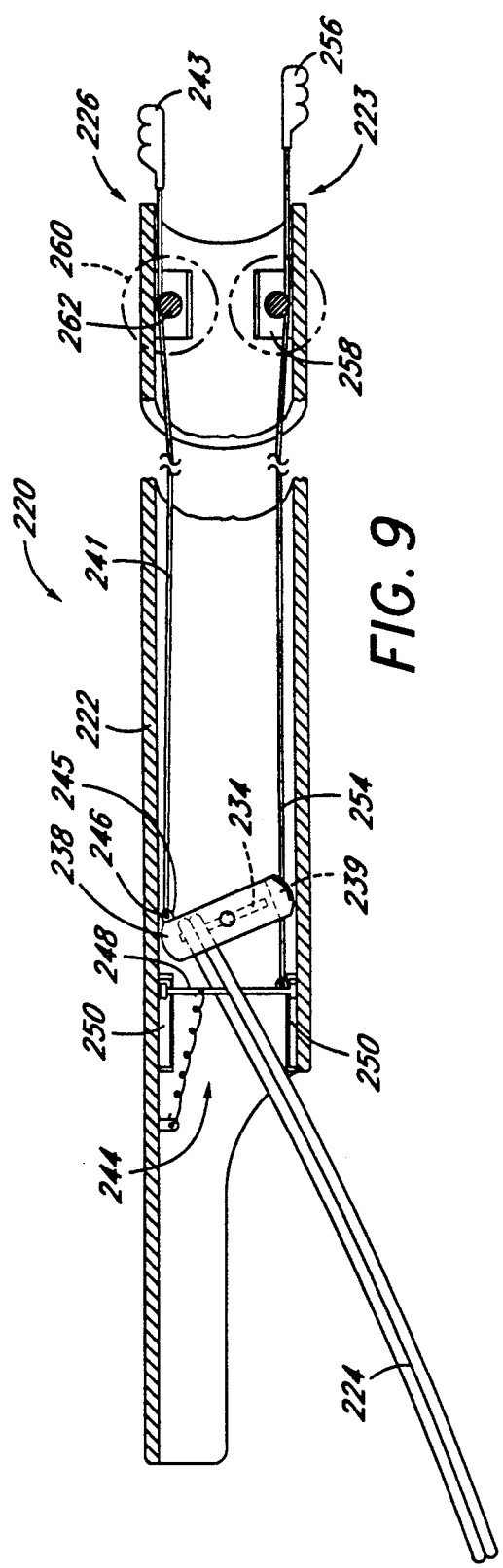

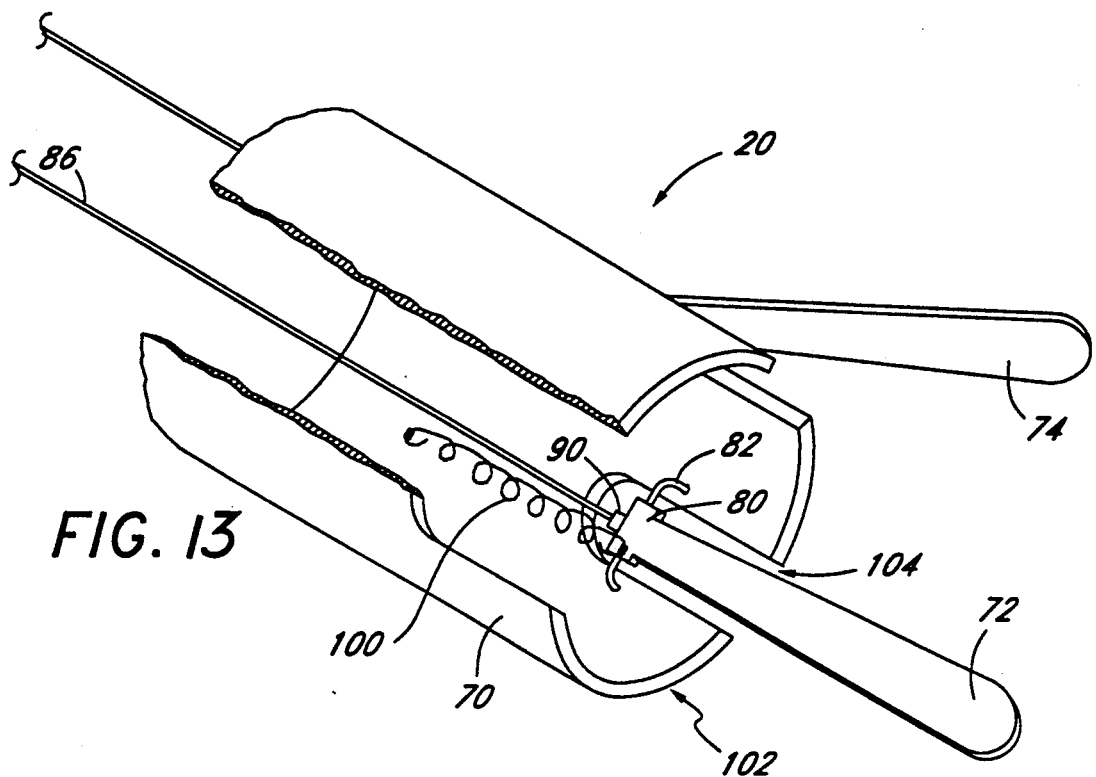
FIG. 13
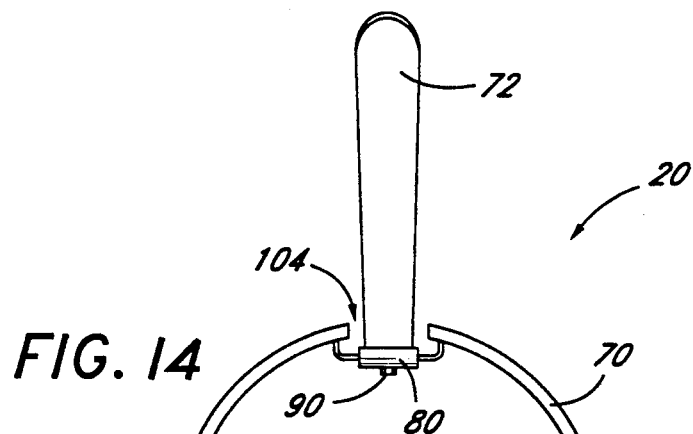
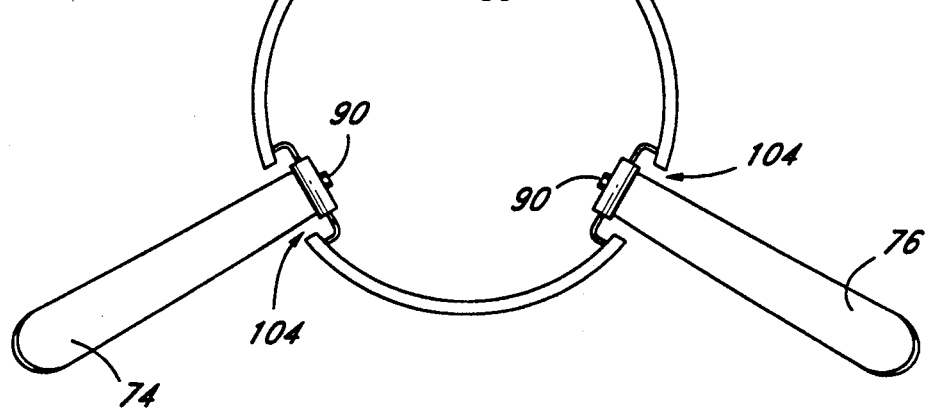
FIG. 14

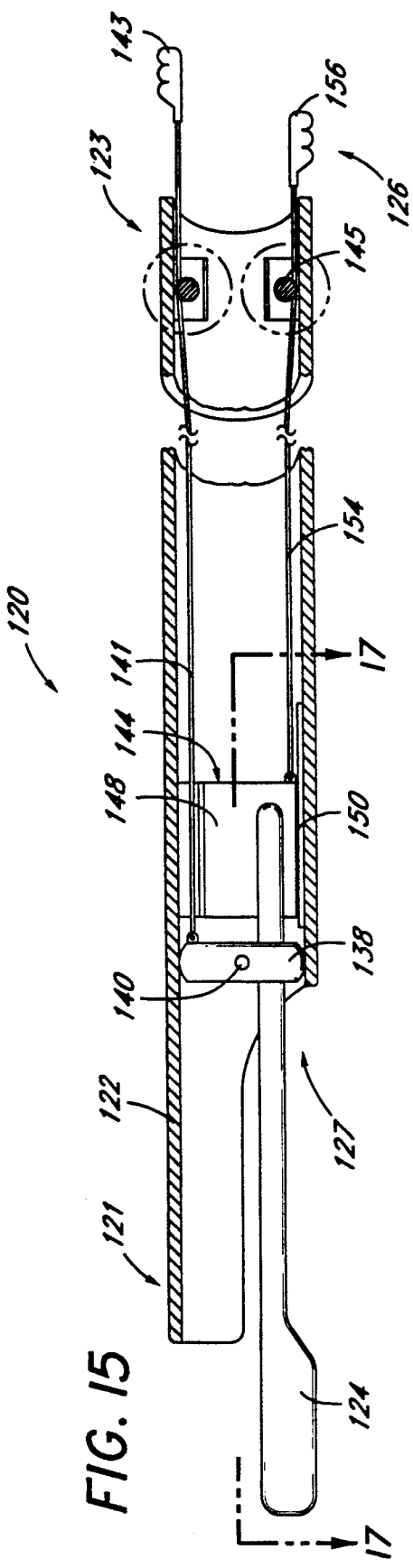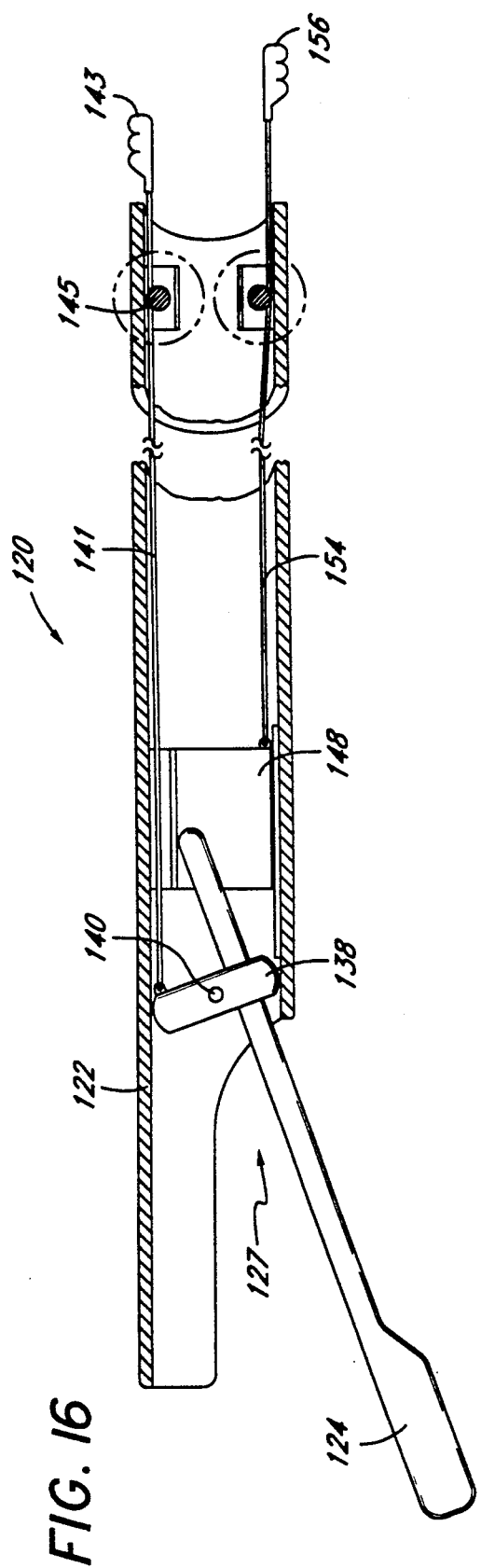

BLADED ENDOSCOPIC RETRACTOR

FIELD OF THE INVENTION

The present invention relates to retractors used in surgery. More specifically, the invention relates to a bladed, expandable endoscopic retractor by which tissue, internal organs, or other internal body parts may be retracted to provide visualization and surgical access during endoscopic procedures.

BACKGROUND OF THE INVENTION

The field of endoscopic surgery has been advancing rapidly in recent years. In this form of surgery, procedures are performed inside of the body of a patient using instruments inserted through small endosurgical ports in the body. The surgery is performed with the aid of an endoscope, which is a thin, tube-like instrument featuring a light source, viewing lenses, and/or various other attachments such as irrigators, scissors, snares, brushes, or forceps. Endoscopes may be flexible or rigid, and normally utilize optic fibers to transmit light to the internal cavity. The surgery is normally viewed by the surgeon through an ocular. Lenses are placed near the tip of the endoscope and the image thereon is transmitted via optic fibers or other lens systems, to the ocular or viewer. Other types of endoscopes utilize optical fibers to transmit electronic signals representing the internal image from the distal lens to a video monitor which is viewed by the surgeon.

This form of surgery allows internal visualization of the body structure without the necessity of excessive dissection of tissue. Typical endoscopes often are in the 5 to 12 mm diameter range and thus require only very small incisions to insert them into the body.

This form of surgery has developed rapidly because of the numerous benefits arising in favor of the patient. Since there is only a small incision to permit entrance of the endoscope, endoscopic surgery results in less trauma to the body and faster patient recovery. For the benefits of endoscopic surgery to arise, however, all aspects of the surgery, such as the initial examination, retraction, and the surgical procedure itself, must be accomplished through small surgical incisions or ports.

The obvious difficulty associated with endoscopic surgery is inadequate visualization of the internal structure required to properly complete the surgical procedure. Endoscopic surgery is thus difficult in areas which are typically difficult to reach, such as the gallbladder. In gallbladder surgery, (or "cholecystectomy") the tissue and organs surrounding the gallbladder are examined with the endoscope and retracted in order to properly expose the organ which is to be removed.

Currently, endoscopic procedures in the abdominal cavity, otherwise known as laparoscopy, often require retraction. Specifically, endoscopic cholecystectomy requires retraction of the liver, which rests directly above the gallbladder. In an open surgery operation, retraction is relatively easy, as the surgery involves the exposure of the entire organ area. In order to obtain the benefits of endoscopic surgery, however, a form of retraction which can be accomplished through ports is necessary.

In an endoscopic procedure involving the gallbladder or other abdominal organs, retraction is currently accomplished by inflating the peritoneal cavity with carbon dioxide. This method of retraction involves creating a small surgical port for introducing a gas source. The gas is introduced into the body through a cannula, and a state of pneumoperitoneum occurs. The gas inflates the peritoneal cavity so as to cause the skin and muscles to separate and rise above various organs and tissue, thus creating the exposure necessary to accomplish the endoscopic surgery.

Several problems are associated with pneumoperitoneal retraction, however. First of all, exposure remains adequate only while the required pneumoperitoneal state remains. Since endoscopic surgery normally requires the introduction of at least the endoscope, and more often several other tools, a number of surgical ports will most likely be created in the body. Each of these ports, which normally use a cannula to keep them open for access, in effect create an exhaust port for the gas. The risk that insufflation pressure may be lost increases the risk that the endoscopic procedure may go awry as adequate exposure for the endoscope is extinguished.

Further, there are many complications which are associated with persistent pneumoperitoneum during an endoscopic procedure. Acute cardiovascular collapse secondary to over-distension of the abdomen, vasovagal reflex activation, cardiac arrhythmia, pneumothorax, subcutaneous emphysema, alteration of large vein venous return, retinal hemorrhage, blindness, carbon dioxide embolism, and general patient discomfort have all been associated with persistent pneumoperitoneum.

Lastly, pneumoperitoneal retraction is effective in retracting only the muscles and tissue from above the organs. The organs themselves are not, to a great extent, retracted from each other.

There is therefore a need for a device and method which provides retraction in conjunction with endoscopic procedures, which is effective in providing adequate visualization and access, and which is safe and has fewer side effects than current methods.

SUMMARY OF THE INVENTION

In accordance with one aspect of the present invention, there is provided a bladed retractor system for use in endoscopic surgery. The invention permits safe and effective endoscopic retraction of internal organs and tissue during endoscopic surgery.

Retraction is accomplished with the present invention through the use of supporting retractor blades which are manipulatable. The blades are movably connected at one end to the inside of a tubular body designed for endoscopic use, and extend therefrom to free ends which may be used to retract the various organs and tissue.

In one embodiment, two blades are movably connected to the insertion or distal end of a tubular body. The body is an elongated member having a small outside dimension for endoscopic use. The body has an opening at its distal end to allow maximum movement of the blades away from the body. The blades, which are primarily flat, thin supporting members, are manipulated by controls located at a control end of the body which is opposite the insertion end of the body. The blades, when in the non-use position, rest substantially directly on top of one another and along a line virtually parallel to the longitudinal axis of the body, thereby aiding in the ease of installing the retractor into the patient's body.

One end of the blades is connected to a vertical pin mounted in a first control member inside the tubular body. The first control member is rotatably attached to the inside of the tubular body. The blades extend from the first control member through a second control member. The second control member is a hollow box shaped member, and rides in a track which extends from the distal end of the body towards the proximal end of the body. A shaft is positioned inside the second control member. The shaft is mounted perpendicular to the blades and extends between them. The blades have a notch in them at a point near their passage through the second control member to accept the shaft.

An actuator is connected to the second control member and extends to a handle at the control end of the body. Movement of the retractor blades is accomplished by manipulating the handle.

In their non-use position, the blades of this retractor embodiment rest primarily on top of one another, as the notch in each blade accepts the shaft of the second control member. The blades lie along the longitudinal axis of the body of the retractor. In this position, the retractor may easily be inserted into the body.

When it is desired to provide retraction, the handle is pushed upon and the second control member is pulled proximally along the track in the body. When this occurs, the shaft in the second control member forces the blades apart. At the same time, the second control member forces the blades downward, away from the longitudinal axis of the body.

A second embodiment of the present invention is substantially similar to the first. However, in this embodiment, the first and second control members are individually manipulatable so as to allow the user to separate and/or extend the blades separately. In this embodiment, the first control member is the same as in the first embodiment, except that an actuator extends from the member to a lockable handle at the control end of the body.

The second control member comprises a shaft which rides in tracks spaced 180° apart at the distal end of the body. The second control member is spring biased towards the distal end of the body. An actuator extends from the second control member to a handle at the control end of the body.

The blades rest in their non-use position on top of one another, along the longitudinal axis of the body, as in the first embodiment. When it is desired to provide retraction, the blades may be extended outwardly through a recess in the distal end of the body and/or spread apart from one another. The actuator, which extends to the first control member, allows the user to move the blades up or down, or, in other words, radially outward in a vertical plane from the longitudinal axis of the body.

The second control member may be actuated by its corresponding handle and the control end of the retractor body. Once again, pulling on the handle moves the second control member proximally, causing the blades to separate.

In a third embodiment of the present invention, the endoscopic bladed retractor comprises a body, controls, and three blades. The body of this retractor is also tubular and long, having a small outer dimension for endoscopic use. The body also has openings at its distal or insertion end to allow the blades to extend outward.

The blades are thin, flat supporting members, each of which is rotatably connected to the body and spaced 120° from one another. Each blade is connected to a rotatable member which allows the blade to extend from a non-use position where the blade is located primarily along a line parallel to the longitudinal axis of the body, to a retraction position where the blade extends outward from the body. Each member has an actuator connected to it which extends to a handle located on the control or proximal end of the body. Further, a locking mechanism is provided to allow each actuator, and thus each blade, to be securely fixed in any position. This retractor, when placed in the body, allows the user to individually select and adjust retraction in the inferior, lateral, and medial directions.

In a fourth embodiment of the present invention, the bladed endoscopic retractor comprises two blades. The body of this retractor is tubular and long, having an opening in the wall of the body at its insertion end to allow the blades to extend therethrough.

The blades are again primarily thin, flat supporting members, both of which extend from a proximal end located inside the body, to a distal end which extends outside of the body of the retractor. The proximal end of the blades is located inside a second control member which is located proximal to the first control member. The blades extend distally from the second control member to engage a first control member. The first control member is rotatably connected to the inside of the distal end of the body.

The blades are connected to one another inside the first control members by a pin. A spring bias is provided between the blades at their proximal ends so that when they are in a non-use position, their distal ends are pressed against one another.

The second control member is movably positioned inside the body, thus allowing the control member to move along the longitudinal axis of the body. The second control member has an internal cut out in which the proximal ends of the blades are mounted.

Actuators are connected to both the first and second control members and extend therefrom to the proximal or control end of the body. Lockable handles are connected to the actuators at their proximal ends.

The blades in this fourth embodiment, like the second embodiment, may be moved independently apart from one another and/or extended away from the longitudinal axis of the body. Advantageously, this embodiment creates less of a risk that tissue inside the body will be damaged. This is because both the first and second control members are located a distance away from the end opening at the distal end of the retractor body. This lessens the chance that tissue which may be pressed into the end of the retractor and caught in the various controls.

In all of the embodiments of the present invention, the blades, when deployed, effectively support the various surrounding organs and tissues by pushing them laterally apart and away from the operating area. In addition, the blades may lift and separate the organs and tissues. Thus, the retractor of the present invention safely provides counter traction for endoscopic surgical procedures. That is, due to a lack of precise depth perception, a significant danger in many forms of endoscopic surgical procedures is cuts or incisions that go too deep may injure vital tissues or organs. Therefore, in order to achieve accuracy in such surgical procedures, there is a need to move neighboring tissue away from the area of incision in order to avoid damage. This is best accomplished by means of counter traction in which the neighboring tissues or organs are moved in one direction by a retractor device while another instrument performs the cut or incision. This movement in opposite directions is referred to as counter traction. In this manner, the retractor blades may also be used to tear or rip apart tissue and organs without the need to use a second instrument, thus serving as a dissector.

Further, there are no obstructions or mechanical structures between the blades when they are extended and separated which might interfere with the surgical procedure. Therefore, a surgeon may clip, cut, or suture in the area between the blades. In this regard, it will be noted that the blades are mounted to the body such that when rotated downward or otherwise extended, the body is tangential to the area of retraction, further avoiding any surgical interference.

Also, the blades are sufficiently rigid so as not to excessively bend or flex when the body is advanced and the blades are used to push organs and tissue out of the way. This allows the blades to be pushed harder against the tissues or organs. This is particularly important, since during use, the blades are essentially cantilevered from the body.

On the other hand, a slight flexing of the blades is desired so as to avoid damage to the tissues or organs. This is provided in the embodiments as described, by providing a slight curvature to the shape of the blades. This curvature not only provides slight flexibility, but can also be used to minimize or maximize retraction surface area. For example, if the blades are concave in the direction of retraction, the effective surface area of retraction is increased. If the blades are convex in the direction of retraction, the surface area of contact between the blades and the tissues and organs is minimized, thereby limiting damage to said tissues and organs.

Therefore, an important advantage of the present invention is that the blades of the present retractor can safely provide counter traction for a wide variety of endoscopic surgical procedures. In addition, the blades of the retractor are devoid of webbing or other mechanical linkages, thus, avoiding damage to the retracted tissue. The blades are also slightly curved in shape to provide limited flexibility and minimize or maximize the retraction surface area.

The present bladed endoscopic retractors provide positive retraction which does not have the dangers associated with continuous peritoneal insufflation. The present invention can be placed with only slight initial insufflation to provide easy insertion of the device. After insertion, retraction can be maintained simply and safely with the blades.

Advantageously, the present retractor is quite small and is easily introduced into the body through only a single small opening. Further, this method of retraction is much more effective in retracting larger organs than the insufflation method. The invention allows the surgeon or assistant to manually retract an organ to any extent necessary, by merely manipulating the position of the blades with the controls. This is in contrast to the insufflation method, where the gas indiscriminately fills the body cavity.

Further, these retractors are adaptable for use on organs of various sizes. By adjusting the blade size and position, the retractor can retract nearly any organ.

Therefore, the retractor of the present invention provides a very advantageous solution to the problems associated with insufflation retraction during endoscopic surgery.

BRIEF DESCRIPTION OF THE DRAWINGS

FIG. 2 is a perspective side view of the first embodiment of the bladed endoscopic retractor of the present invention illustrating the blades thereof in their non-separated, non-extended (non-rotated) position, suitable, for example, for endoscopic insertion.

FIG. 3 is a partial enlarged side view of the distal end of the first embodiment.

FIG. 4 is a partial enlarged top view of the distal end of the present invention illustrating the blades in a slightly separated position.

FIG. 8 is a partial side view of the second embodiment of the present invention.

FIG. 9 is a side view of the second embodiment of the present retractor illustrating the blades tilted downwardly away from the longitudinal axis of the retractor body.

FIG. 13 is a partial enlarged perspective end view of the third embodiment of the present invention.

FIG. 14 is an enlarged end view of the retractor of FIG. 13 with the blades extended.

FIG. 15 is a partial side view of the fourth embodiment of the present invention.

FIG. 16 is a partial side view of the retractor of FIG. 15 with the blades in their extended retraction position.

DETAILED DESCRIPTION OF THE ILLUSTRATED EMBODIMENT

Figure 1:
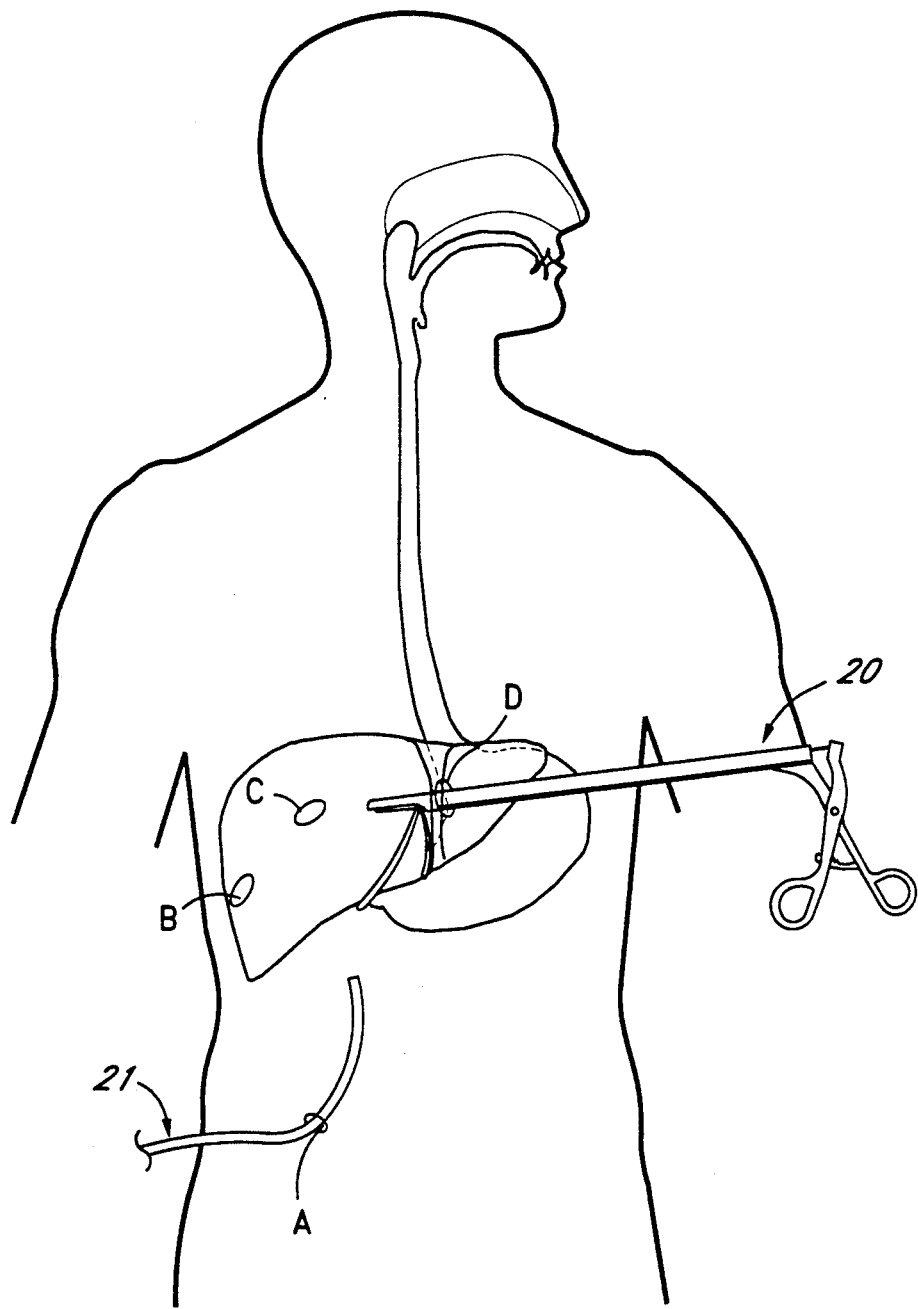
FIG. 1 is a schematic view illustrating the manner in which the retractor of the present invention may be inserted through a small surgical port for use in endoscopic surgery.

Referring first to FIG. 1, there is shown a schematic view of a patient undergoing endoscopic surgery. Thus, a small surgical port A is shown through which an endoscope 21 is inserted. This allows the surgeon to view the internal tissues and organs in the surgical area. Other surgical devices (not shown) may be inserted through similar surgical ports B and C in order to perform the desired procedure.

The retractor 20 of the present invention is shown inserted through yet another port D so as to be in the surgical region. Thus, the retractor can be used to safely manipulate tissues or organs during surgery. It should be noted, however, that the principles of the present invention are not limited to any particular surgical procedure but may be applied to a wide variety of procedures and applications.

First Embodiment

Referring to FIG. 2, there is shown one embodiment of the bladed endoscopic retractor 20 of the present invention. FIG. 2 discloses a body 22 having various retractor blades 24 extending therefrom which are manipulatable by various controls 26. As illustrated, the body 22 of the bladed endoscopic retractor 20 is a tube. The body 22 may be of other shapes; however, a circular cross-section is preferred since it is most easily inserted into a cannula. The outer diameter of the body 22 is preferably minimized so that the incision size required to insert the endoscopic retractor and the trauma to the patient's body is also minimized. The length of the body 22 is dependent primarily upon the type of procedure in which the bladed endoscopic retractor 20 is to be used.

The body 22 has a proximal or control end 23 and a distal or insertion end 25. The distal end 25 of the body 22 has an elongated opening 27 (FIG. 3) extending from the end in a proximal direction along the underside of the body 22. The proximal end 23 is the site of the various controls 26 which operate the retractor. The body 22 is preferably made of a material, such as stainless steel, which will remain free from degradation, is easily sterilized, and is biocompatible.

Blades 24 are mounted within the body 22 near the distal end 25 so as to extend therefrom. The blades 24, as shown in FIG. 4, are primarily flat, elongated members. The blades 24 may, of course, take on a variety of shapes depending upon the particular surgical procedure, solong as they will not cause trauma to internal tissues or organs, either during insertion or use. The blades 24 taper at their proximal end 32 (FIG. 3) where they are movably connected to the body 22. The blades 24 each have a notch 21 (FIG. 5) at a point near their exit from the body 22. The notches 21 are slightly elongated and taper distally to a point where each notch is wide enough to accept a shaft 48 as described below in connection with FIG. 5.

Figure 5:
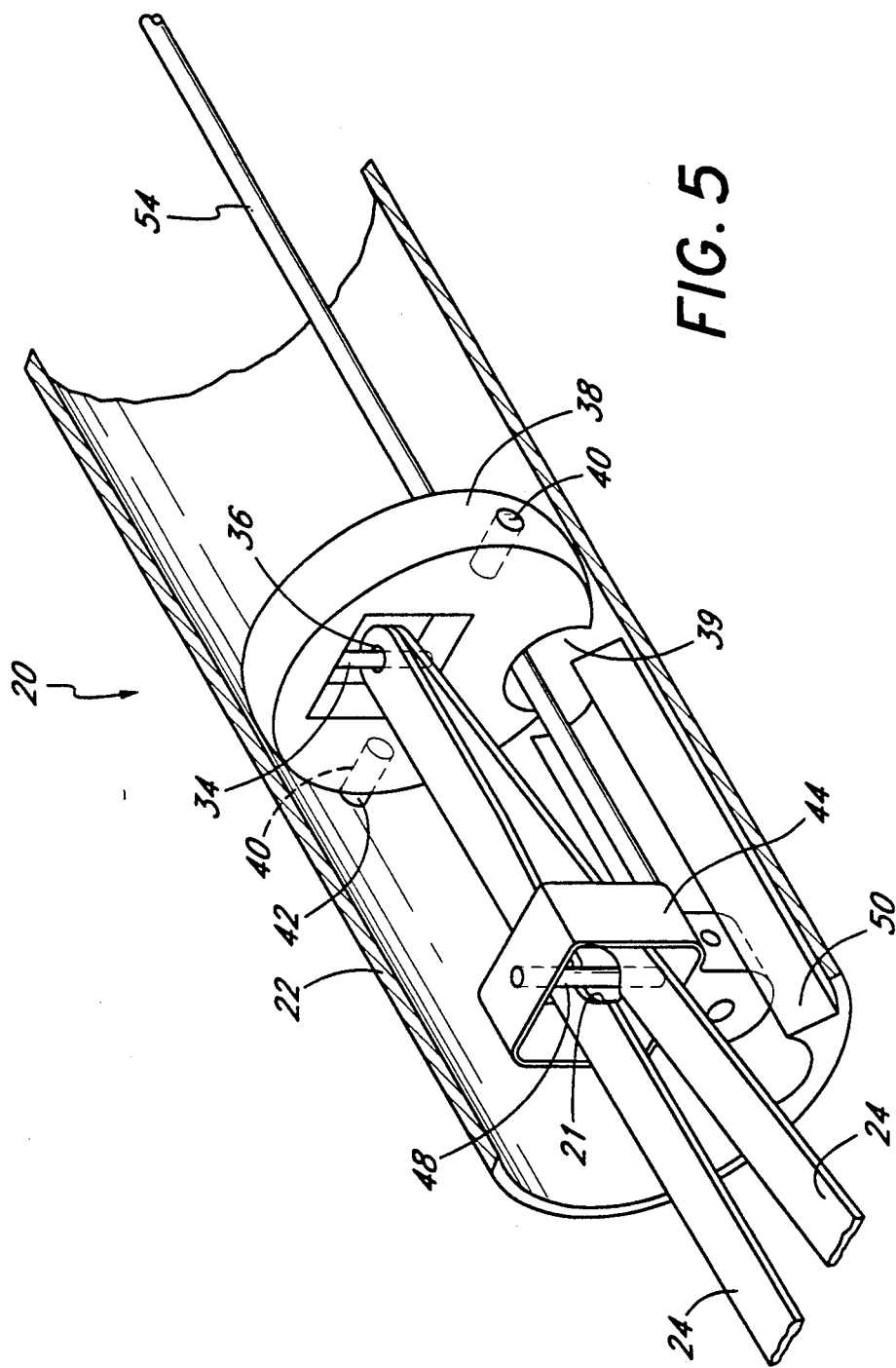
FIG. 5 is a partial enlarged perspective view of the distal end of the present invention showing the blades in a slightly separated, non-extended position.
Figure 6:
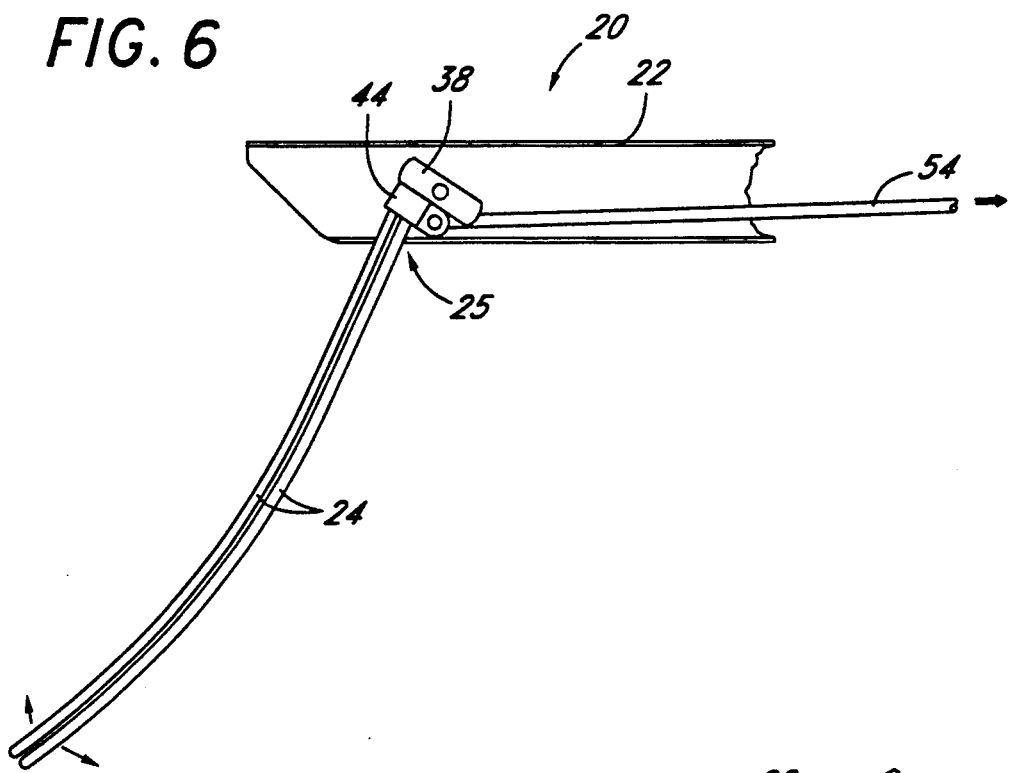
FIG. 6 is an enlarged side view of the distal end of the present invention showing the blades in their separated, extended retraction position.

The blades 24, as illustrated in FIGS. 2-5, rest in their non-use position on top of one another. As shown in FIG. 5, a pin 34 passes vertically through holes 36 in the proximal end of the blades 24. The pin 34 is, in turn, mounted to a first control member 38. The first control member 38 comprises a disc which is relatively thick and substantially cylindrical. The disc is housed inside the body 22 near its distal end 25. The diameter of the first control member 38 is less than the inner diameter of the body 22, so that it may rotate in the body 22. The first control member 38 has a rectangular portion cut out of its middle section, inside of which the pin 34, which supports the blades 24, is mounted. The first control member 38 also has a small arch 39 cut out of its bottom surface thus allowing the passage of an actuator 54, which will be described in more detail later.

Pins 40 (FIG. 5) are mounted opposite one another on each side of the first control member 38 and perpendicular to the direction that the pin 34 is mounted. The pins 40 extend from the first control member 38 into small holes 42 in the body 22. This mounting allows the first control member 38 to rotate about the pins 40.

A second control member 44 is mounted distally of the first control member 38. This second control member 44 is a hollow square body having a shaft 48 mounted therein. The shaft 48 is oriented perpendicular to the blades 24. As can be seen in FIG. 5, the blades 24 pass through the second control member 44 on either side of the shaft 48. Referring to FIG. 3, it can be seen that the height of the second control member 44 is less than the height at which the blades 24 are connected at their proximal ends 32 to the first control member 38. This differential provides for the generation of a movement acting about connection pin 40, as described in more detail below.

As illustrated in FIG. 5, the second control member 44 rides in a track 50 in the inside of the body 22. The mounting of the second control member 44 on the track 50 allows the control member 44 to move along the inside of the body 22 in a direction parallel to the longitudinal axis of the body 22. An actuator 54 is attached to the second control member 44 at its lower end on the proximal side, extends through the arch 39 in the first control member 38, and continues through the body 22 to its proximal end 23, where it is attached to a handle 56.

Referring to FIG. 2, handles 43, 56 are both located outside of the proximal end 23 of the body 22. The handles 43, 56 as illustrated are elongated and are of a dimension sufficient to permit manipulation by hand. Each handle 43, 56 is preferably made from stainless steel. Handle 43 is connected securely to the body 22. Handle 56 is rotatably connected to handle 43 with a pin 66. Handle 56 is also connected to actuator 54 by a pin 41. The handles 43, 56 could, of course, be made of plastic or other durable material and could be attached to the actuator 54 with glue, screws or other means.

A notched member 68 extends from handle 43 towards handle 56. The notched member 68 is slightly curved and lies directly alongside handle 56. The notches in the notched member 68 are engaged by a pin (not shown) extending outwardly from handle 56. In this manner, handle 56, and its corresponding actuator 54, may be locked into any position using the pin and notch lock.

Referring to FIGS. 3-7, the operation of the retractor 20 as used to provide retraction in a cholecystectomy procedure will now be described. The retractor 20 is inserted into the body. This is normally accomplished by introducing a state of slight pneumoperitoneum, and then sliding the retractor 20 into the body through a cannula. When the retractor 20 is initially inserted, the blades 24 should be in their non-use position; that is, aligned parallel to the axis of the body 22 with one on top of the other (FIG. 3). As is now evident, the notches 21 accommodate the shaft 48 in the second control member 44 so as to allow the blades 24 to lie nearly directly on top of one another in their non-use position. This is particularly advantageous since the blades 24 may thus be closed on top of one another, thus limiting the size of the cannula necessary to accept the retractor 20.

Once the retractor 20 is in the body, it may be properly aligned and operated. Placement of the retractor 20 may be aided by an endoscope. Once in place, handle 56 is pushed away from handle 43 along the notched member 68. In this fashion, actuator 54 pulls the second control member 44 towards the control end 23 of the body 22 along the track 50. When this occurs, the shaft 48 (FIG. 5) in the second control member 44 forces the blades 24 apart. At the same time, because the height of the second control member 44 is lower than the connection of the blades 24 to the first control member 38, the blades 24 are forced downwardly and away from the longitudinal axis of the body 22 due to the movement force mentioned above. As can be seen from FIGS. 5–7, the rotation of the blades 24 away from the longitudinal axis of the body 22 is facilitated by the rotational mounting of the first control member 38 on the pins 40. In this embodiment, therefore, operation of the actuator 54 simultaneously spreads the blades apart and pushes them downward away from the longitudinal axis of the body 22. Deployment of the blades into this retraction position is accomplished by this simultaneous spreading of the blades 24 (FIG. 7) and their downward rotation (FIG. 6) away from the longitudinal axis of the body 22.

Figure 7:
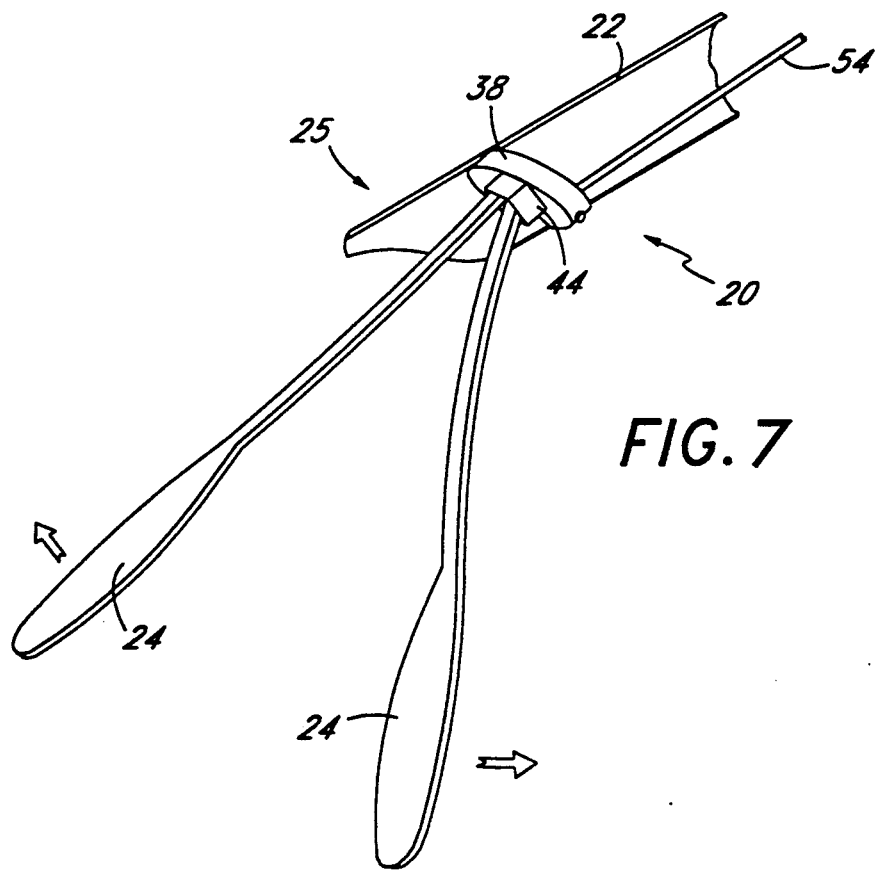
FIG. 7 is an enlarged perspective view of the distal end of the present invention showing the blades in their separated, extended, retraction position.

Therefore, the blades of the present retractor can assume a variety of positions with the degree of spreading being proportional to the rotation of the blades. When the appropriate deployment of the blades is accomplished, they can be locked in place for safe retraction. As shown in FIG. 7, the blades 24 of the present retractor are relatively blunt and without sharp edges in order to avoid damage to the retracted tissue. In addition, as well illustrated in FIG. 7, there are no connections or mechanical linkages located between the blades which would pinch or lacerate tissues. Therefore, the present retractor safely provides counter traction for many types of endoscopic surgical procedures in the peritoneal area.

Once the surgical procedure has been completed and it is desired to remove the retractor 20, handle 43 is pulled in the direction of handle 56. Pulling handle 43 in this direction forces the second control member 44 towards the distal end 25 of the body 22. This allows the blades 24 close together, to a point where the shaft 48 is once again resting in the notches 21 and the blades 24 are nearly on top of one another. At the same time as the blades 24 are closed towards one another, because the second control member 44 has moved away from the first control member 38, causing the blades 24 to rotate back towards the longitudinal axis of the body 22. At this time the retractor 20 may be removed from the body.

Second Embodiment

A second embodiment of the retractor 220 is illustrated in FIGS. 8–12. This embodiment is similar to the first embodiment; however, in this embodiment, first and second control members 238, 244, are independently manipulatable. Thus, the degree of separation or degree of spreading of the blades can be adjusted for retraction independently of the degree of downward rotation or extension of the blades away from the longitudinal axis of the body 222. In addition, these adjustments for separation and downward rotation can be accomplished one at a time or simultaneously, if desired.

As illustrated in FIG. 8, the retractor 220 comprises the body 222 having retractor blades 224 extending therefrom which are manipulatable by various controls 226.

The body 222 is similar in construction to the body 22 described above, having similar dimensions and materials. The body 222 has a proximal or control end 223 and a distal or insertion end 225. The body 222, once again, has a lower elongated recess 227 extending from the distal end 225 towards the proximal end 223. The various controls 226 are again located at the proximal end 223 of the body 222.

The blades 224 extend from the distal end 225 of the body 222, and are similar in shape and material to those described above. A notch 221 (FIG. 12) is located in each of the blades 224 to facilitate the introduction of a shaft 248, as described more fully below.

Figure 10:
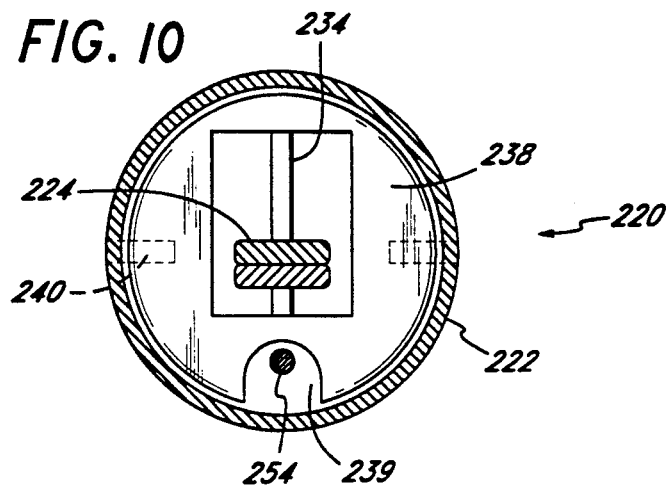
FIG. 10 is an end view of the retractor of the second embodiment illustrating the blades in their non-extended position.
Figure 11:
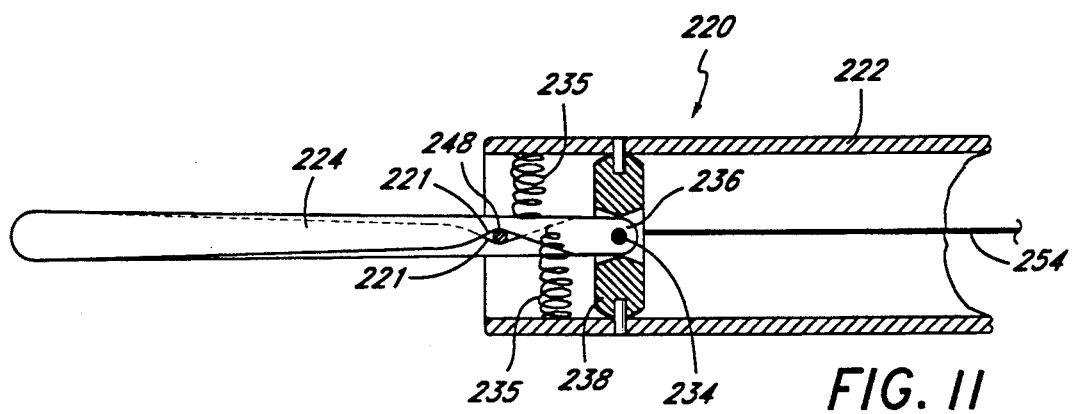
FIG. 11 is a partial top view of the second embodiment of the present retractor, illustrating the blades in their non-extended position.

The blades 224, as illustrated in FIGS. 8, 10 and 11, rest in their non-use position on top of one another. A pin 234 passes vertically through holes 236 in the proximal end of the blades 224. The pin 234 is, in turn, mounted to a first control member 238. Springs 235 (FIG. 11) are attached to each blade 224 and to the inside of the body 222 so as to bias the blades 224 towards the center of the body 222 and against the shaft 248.

The blades 224 are connected at their proximal ends to a first control member 238 which is substantially similar to that described above, and thus will not be redescribed here.

An actuator 241 (FIGS. 8 and 9) is mounted to the proximal side of the first control member 238 at a point near the top middle of the control member 238. The actuator 24 is preferably a long rod which extends from a handle 243 at the proximal end 223 of the body 222, to a mounting member 245 on the first control member 238. The mounting member 245 is, as shown in FIG. 8, substantially U-shaped. The actuator 241 is attached to the mounting member 245 with a pin 246 which passes through the actuator 241 and the mounting member 245.

A second control member 244 (FIGS. 8 and 9) is mounted distally of the first control member 238. This second control member 244 comprises a shaft 248 mounted at both ends in a track 250. The ends of the shaft 248 slide along the tracks 250, which are T-shaped grooves formed on the inside of the body 222. The tracks 250 are spaced 180° from one another. The shaft 248 extends between the tracks 250 and passes in between the blades 224. As can be seen in FIG. 11, when the shaft 248 is at its furthest distal point in the tracks 250, the shaft passes through the notches 221 in the blades 224.

The mounting of the shaft 248 in the tracks 250 allows the shaft 248 to move along the inside of the body 222 in a direction parallel to the axis of the body. A spring 252 mounted on the distal side of the second control member 244 biases the shaft 248 toward its furthermost distal point on the tracks 250. As illustrated in FIG. 8, the spring 252 is attached to the inside of the body 222 at a point distal of the tracks 250.

An actuator 254 (FIG. 9) is attached to the shaft 248 at its lower end on the proximal side, extends through the arch 239 (FIG. 10) in the first control member 238, and continues through the body 222 to its proximal end 223, where it is attached to a handle 256.

Referring to FIGS. 8 and 9, the actuators 241, 254 each extend through a guide member 258. The guide members 258, as shown, are U-shaped members attached to the inside of the body 222 near its proximal end. The guide members 258 each surround its corresponding actuator 241, 254, thus forming a tube through which the actuator 241, 254 passes.

Knobs 260 are attached to threaded shafts 262 which pass through circular holes (not shown) in the body 222. The shafts 262 engage threaded bores in each guide member 258. Each knob 260 may be tightened into the guide member 258 so as to force the actuator 241, 254 therein against the other side of the guide member 258, thus preventing the actuator 241, 254 from moving. Therefore, the position of the blades 224 may be locked into place for use during the surgical procedure.

Referring to FIGS. 8-12, the operation of the retractor 220 as used to provide retraction in a typical surgical procedure will now be described. The retractor 220 is inserted into the body. This is normally accomplished by introducing a state of slight pneumoperitoneum, and then sliding the retractor 220 into the body through a cannula. When the retractor 220 is placed, the blades 224 should be in their non-use position shown in FIG. 8; that is, aligned parallel to the axis of the body 222 with one on top of the other. As is now evident, the notches 221 accommodate the shaft 248 so as to allow the blades 224 to lie nearly directly on top of one another in their non-use position. This is particularly advantageous since the blades 224 may thus be closed on top of one another, thus limiting the size of the cannula necessary to accept the retractor 220.

Figure 12:
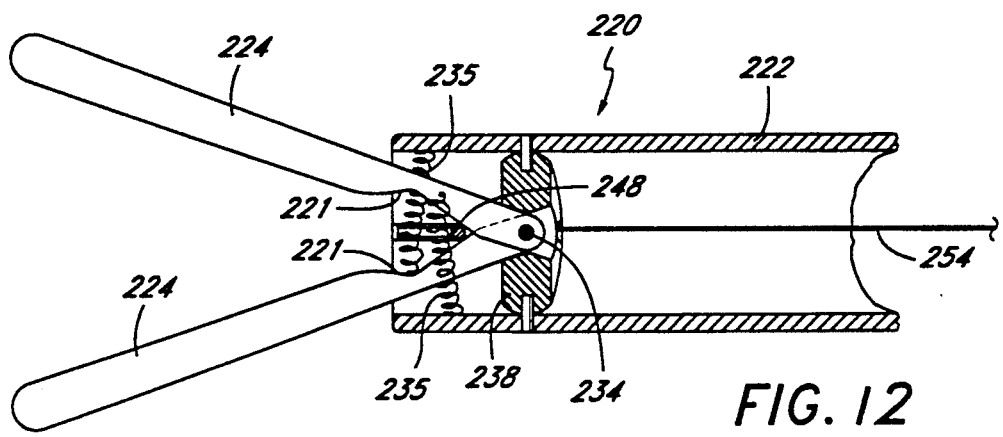
FIG. 12 is a partial top view of the second embodiment of the present retractor, showing the blades in their separated, extended retraction position.

Once the retractor 220 is in the body, it may be properly aligned and operated. Placement of the retractor 220 may be aided by an endoscope. The blades 224 may be spread apart by manipulating the second control member 244. The knob 260, which tightens against the actuator 254 connected to the second control member 244, is loosened. The handle 256 is pulled to move the actuator 254 proximally, thus the shaft 248 is moved towards the proximal end of the body 222. As shown in FIG. 12, this forces the shaft 248 proximally between the blades 224, causing them to separate. Once the blades 224 have been separated by the proper distance, the knob 260 is tightened to lock the actuator 254 and the blades 224 into place.

The blades 224 may either be rotated from the longitudinal axis of the body 222 after the blades 224 have been separated, or the above separation step may be omitted. To extend the blades 224, as illustrated in FIG. 9, the knob 260 which fixes actuator 241 is loosened. The handle 243 on actuator 241 is pushed distally, forcing the first control member 238 to rotate. The control member 238, in turn, rotates the blades 224 away from the longitudinal axis of the body 222 through opening or recess 227. The knob 260 may then be tightened to fix the actuator 241 and the blades 224 in this extended position.

The importance of the opening 227 in the distal end 225 of the body 222 is now apparent. The opening 227 is of such a width and length to allow the blades 224, which are spaced apart when being used, to move a greater distance radially outward than would be possible without opening 227. Of course, a recess could be provided in the top of the body 222; however, merely by turning the retractor 220 over, any "upward" retraction can easily be accomplished. It should be noted that if the blades 224 are moved downward before they are spaced apart, the range of motion is limited, since the blades 224 will contact the track 250 which extends towards the distal end 225 of the body 222 (FIG. 9). Merely by adjusting the distance of the first control member 238 from the distal end 225 of the body 222, the angle at which the blades 224 extend from the body 222 before contacting the track 250 may be varied.

When it is desired to remove the retractor 220, the blades 224 are closed together. This is accomplished by loosening the knob 260 connected to the actuator 254. The spring 252 causes the shaft 248 to move distally until it falls into the notches 221 in the blades 224, at which time the blades 224 will be closed together. It will be noted that the springs 235 bias the blades 224 toward one another so that they are closed together at the same time as the shaft 248 moves into the notches 221. The knob 260 connected to the actuator 241 is then loosened so that the blades 224 move back to a line parallel to the longitudinal axis of the body 222. This accomplished by pulling the handle 243 so that the actuator 241 moves in a proximal direction, causing the first control member 238 to assume a more vertical position, thereby bringing the blades 224 into horizontal alignment with the body 222 of the retractor 220. At this time, the retractor 220 may be removed from the body through the cannula.

Third Embodiment

In another or third embodiment illustrated in FIGS. 13 and 14, the body 70 houses three blades 72, 74, 76. A first blade 72 is designed to provide medial retraction, a second blade 74 is designed to provide inferior retraction, and a third blade 76 is designed to provide lateral retraction. All three blades 72, 74, 76 are preferably flat, thin members. The exact length, width and shape of each blade 72, 74, 76, may, of course, be individualized for specific procedures. Further, it is contemplated that only one or two, or four or more blades may be utilized.

The three blades 72, 74, 76 are all mounted and controlled alike, the three blades being spaced 120° from one another in the body 70 near its distal or insertion end 102. Therefore, only one mounting and control will be described herein.

The first blade 72 is attached at one end to a block 80, comprising a small rigid member. A U-shaped mounting pin 82, best seen in FIG. 14, passes through a bore (not shown) in the block 80. The pin 82 is connected at each of its ends to the inside of the body 70. This mounting allows the block 80, and thus the blade 72, to rotate about the pin 82. It is contemplated that the block 80 may be formed as part of the blade 72 so that the blade 72 in effect has a mounting end (see FIG. 13).

An actuator 86 is attached to the side of the block 80 facing the center of the body 70 (FIG. 14). A pin (not shown) passes through the actuator 86 and a mounting member 90 on the block 80 configured to allow the actuator 86 to move relative to the block 80. The actuator 86 extends the length of the body 70 to a handle (not shown), similar to that described above in the second embodiment, located at the proximal or control end of the body 70. The actuator 86, as described in the second embodiment, passes through a tubular guide member (not shown). A threaded shaft attached to a knob like that described in the above embodiment may again be used to lock the actuator 86, and thus prevent the blade 72 from moving.

A spring 100 (FIG. 13) is mounted at one end of the block 80 on the same side as the actuator 86. The spring 100 is mounted to the body 70 at its other end, and biases the blade 72 towards a position where the blade 72 lies along a line parallel to the longitudinal axis of the body 70.

The body 70 is shaped primarily like the body 22 described above. In this embodiment, however, there are three openings 104 located at the distal end 102 of the body 70. The openings 104 extend from the distal end 102 along the body 70 towards its proximal end just past the block 80. The openings 104 provide an area for the blades 72, 74, 76 to extend radially out of the body 70.

The operation of this third embodiment of the retractor 20 will now be described in conjunction with FIGS. 13 and 14.

The retractor 20 is inserted into the patient's body as described above. The blades 72, 74, 76 of the retractor 20 will be aligned along the axis of the retractor body 70 at this time. Once the retractor 20 is inside the patient's body, the blades 72, 74, 76 may individually be extended so as to retract tissue and organs. A given blade 72, 74, 76 is easily manipulated by using its respective actuator 86. The locking knob is loosened so that the actuator 86 may be pushed inwardly using the handle on its end. This causes the block 80 to rotate about the pin 82, causing the blades 72, 74, 76 to move away from the longitudinal axis of the body 70 through its corresponding opening 104. The locking knob is then tightened to fix the position of the blade 72, 74, 76. As can be seen, all three blades 72, 74, 76 may be advantageously moved independently of one another. This allows the user to customize retraction in the lateral, inferior and medial directions.

The retractor 20 may be removed simply by loosening the locking knob, and allowing the spring 100 to bias the blades 72, 74, 76 back towards the axis of the body. When all blades 72, 74, 76 have returned to this position, the retractor 20 may be removed.

Fourth Embodiment

Yet another embodiment of the present invention will now be described in conjunction with FIGS. 15-18. The bladed endoscopic retractor 120 in this embodiment is similar to the first embodiment described above, and comprises a body 122 and various retractor blades 124 extending therefrom which are manipulatable by various controls 126.

As illustrated in FIG. 15, the body 122 of the retractor 120 is a tube. The body 122 is similar in shape and dimension to that described in the above embodiments, and may be made of the same materials. The body 122 once again has a proximal or control end 123 and a distal or insertion end 121. The distal end 121 of the body 122 preferably has one large opening or recess 127 extending from the end proximally along the body 122. The proximal end 123 of the body 122 is the site of the various controls 126 which operate the retractor.

Figure 17:
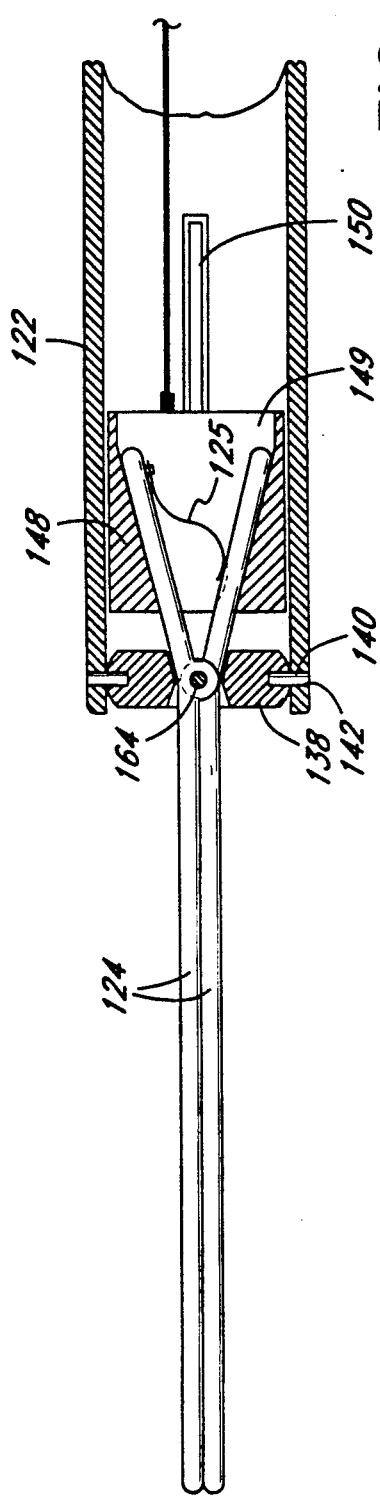
FIG. 17 is a partial top view along LINE 17—17 of the distal end of the retractor of FIG. 15.
Figure 18:
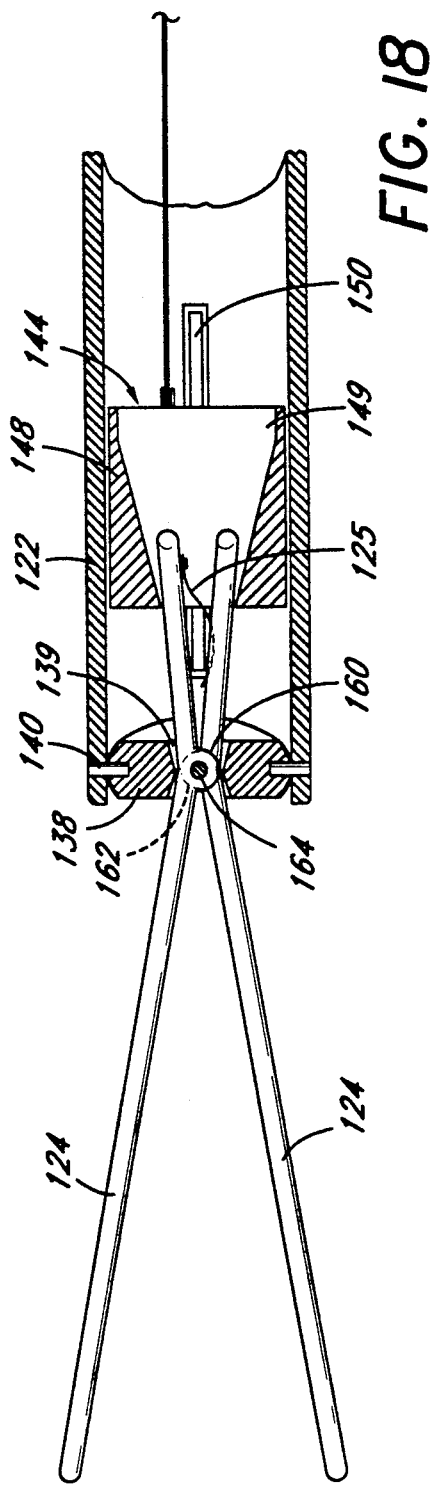
FIG. 18 is a partial top view of the distal end of the retractor of FIG. 15 with the blades in their separated, extended retraction position.

As shown in FIGS. 15 and 18, the blades 124 are mounted within the distal end 121 of the body 122 and extend therefrom. The blades 124 have nearly the same shape and dimension as those in the above embodiments, except that in this case their proximal ends bend outwardly towards the sides of the body 122, as shown in FIGS. 17 and 18. An S shaped spring 125 is mounted in between the blades 124 at their proximal ends. The spring 125, as illustrated in FIGS. 17 and 18, is made of flat spring steel and is securely fastened to the end of one of the blades 124, extending distally until it contacts the other blade. The spring 125 has the tendency to force the proximal ends of the blades 124 apart, and thus the distal ends of the blades 124 together.

As illustrated in FIGS. 15 and 17, the distal ends of the blades 124 rest in their non-use position against one another. The blades 124 extend from their distal ends located outside the body, into the distal end 121 of the body 122 and then pass through a first control member 138 and terminate at their proximal ends inside a second control member 144. A pin 164 passes through holes in the blades 124 at a point between the first and second control members 138, 144. The pin 164 is designed such that the blades 124 are securely retained on the pin 164, and yet the blades 124 have space on the pin 164 to allow them to move slightly. This may be accomplished by having the holes in the blades 124 be of a slightly larger diameter than the diameter of the pin 164, while having the ends of the pin 164 large enough to prevent the removal of the blades 124.

The first control member 138 is a disc which is relatively thick and substantially cylindrical. The first control member 138 is housed inside the body 122 near its distal end 121 and just proximal to the proximal end of the opening 127 in the body 122. The first control member 138 is primarily of the same shape and dimension as the first control member 38 described in the first embodiment. The first control member 138 has an hourglass cutout 139 (FIG. 18) of its middle, through which the blades 124 extend. The height of the cutout 139 is nearly the same as that of the blades 124. The width of the cutout 139 is such that it allows the blades 124 to move apart from one another.

The blades 124 are connected to one another and the first control member 138. One blade 124 has a U shaped member 160 which faces towards the other blade 124. The other blade 124 has a flange 162 which extends into the opening of the U shaped member 160. A pin 164 is located inside the cutout 139 in the first control member 138 and oriented perpendicular to the axis of the blades 124. This pin 164 extends through holes in the U shaped member 160 and flange 162.

Once again, pins 140 are mounted opposite one another on each side of the first control member 138 and perpendicular to the axis of the blades 124. The pins 140 extend from the first control member 138 into small holes 142 in the body 122. This mounting allows the first control member 138 to rotate about the pins 140 inside the body 122.

As illustrated in FIGS. 15 and 16, an actuator 141 is mounted to the proximal side of the first control member 138 at a point near the top middle of the member 138. The actuator 141 is preferably a long rod which extends from a handle 143 at the proximal end of the body 122 to a locking member 145 which is the same as that as disclosed in the second embodiment detailed above.

The second control member 144 is, as stated above, mounted proximally of the first control member 138. This second control member 144 comprises an actuating block 148 mounted on a track 150.

The actuating block 148 is primarily circular on its outer surface. As seen in FIGS. 17 and 18, a cutout 149 is provided in the block 148 to allow the acceptance of the proximal ends of the blades 124. The cutout 149 extends, from the distal facing side of the actuating block 148, widening as it extends through the block where, near the proximal facing side of the block, the cutout 149 has a fixed size. The cutout 149 is of a height such that it allows the blades 124 to move up and down therein without contacting the top or bottom of the cutout 149.

As illustrated in FIGS. 15 and 17, the proximal ends of the blades 124 extend into the cutout 149 in the actuating block 148. The shape of the proximal ends of the blades 124 allows the blades 124 to conform to the walls of the cutout 140 inside the block 148.

As stated above, the actuating block 148 is mounted upon a track 150. The track 150 runs parallel to the blades 124. An actuator 154 is mounted to the lower proximal face of the actuating block 148, and extends to a handle 156 located at the proximal end 122 of the body 123 (FIG. 15).

The handles 143, 156 and their lockable mounting are primarily the same as that described in the second embodiment above, and therefore they will not be described here.

The operation of the retractor 120 will now be described. The retractor 120 is installed into the body in the area to be retracted with the blades 124 in their non-actuated position corresponding to that where the distal ends of the blades 124 are located side by side against one another and along the longitudinal axis of the body 122 (FIGS. 15 and 17).

When it is desired to move the blades 124 in order to provide retraction, the various handles 143, 156 are used. In order to move the blades 124 apart from one another, the second handle 156 is pulled, forcing the second control member 144 along the track 150 towards the proximal end of the body 123. This causes the proximal ends 123 of the blades 124 to be pressed/towards one another as the width of the cutout 149 in the actuating block 148 of the second control member 144 decreases in size, as seen in FIG. 18. This pressing of the blades 124 compresses the spring 125. As illustrated in this figure, the blades 124 are allowed to spread apart from one another through their rotatable connection at pin 164 in the first control member 138.

When it is desired to move the blades 124 up or down away from the longitudinal axis of the body 122, the first handle 143 is used. The user pushes upon the first handle 143, forcing the first control member 138 to rotate about the pins 140. This causes the blades 124, which pass through the cutout 139 in the first control member 138 to be rotated downwardly. The distal ends of the blades 124 move away from the longitudinal axis of the body 122, extending through the opening 127 in the body 122, as seen in FIG. 16.

As can be seen, the opening 127 allows the blades 124 to move to a greater extent than is possible without the opening. If the first control member 138 is moved such that it pushes the blades 124 upward, the movement of the blades 124 is limited by the body 122. While an opening could be provided on both the top and bottom of the body 122, this would tend to compromise the structural integrity of the distal end 121 of the body 122. This same function can be accomplished merely by having one opening and turning the device over to provide retraction in the upward direction.

The above arrangement allows the blades 124 to independently be spread apart or moved up or down to any extent. This advantageously allows retraction to be individualized in either or both directions for the specific use to which the retractor 120 is being put. Lastly, this retractor 120 has numerous benefits. For example, it has no control member located very near the distal 121, open end of the body 122. This prevents tissue or other body material which might protrude slightly into the end of the body 122 from being damaged through operation of the retractor 120. Further, the mechanical operation of this retractor 120 is somewhat less complicated, allowing the cost of the device to be reduced.

It will be understood that the above described arrangements of apparatus and the methods therefrom are merely illustrative of applications of the principles of this invention and many other embodiments and modifications may be made without departing from the spirit and scope of the invention.

What is claimed is:

1. An endoscopic retractor, comprising:
a body having a distal end, a proximal end, and a longitudinal axis, said distal end being inserted into the body of a patient and said proximal end remaining outside of said body, said distal end being undercut and defining a terminal plane for said body;
at least two blades, each having a distal end and a proximal end, said proximal end being mounted for rotation on said distal end of said body, said distal end extending beyond said terminal plane of said body, said blades being closely aligned and conformed with one another to assume a longitudinal insertion position;
a control member aligned with the proximal end of said blades; and
an actuator connected to said control member whereby movement of said actuator causes said control member to engage the proximal ends of said blades, whereby said blades are rotated to an extended position to provide retraction in a wide variety of angular positions with respect to the longitudinal axis of said body.

2. The retractor of claim 1, wherein said movement of said control member is in a proximal direction.

3. The retractor of claim 1, wherein said control member is biased in a distal direction to cause said blades to return to the insertion position.

4. The retractor of claim 1, wherein said control member engages one of said blades, causing both of said blades to rotate to the extended position.

5. The retractor of claim 1, wherein said control member further comprises a shaft inserted between said blades, whereby movement of said control member simultaneously causes said distal ends of said blades to separate.

6. The retractor of claim 1, wherein said blades are biased toward their aligned insertion position.

7. The retractor of claim 1, wherein said control member engages said blades at a point not along a line passing through a connection of said blades with said body and parallel to a longitudinal axis of said body, whereby movement of said actuator causes a moment about said control member whereby said blades are rotated.

8. An endoscopic retractor, comprising:
an elongate body having a distal end and a proximal end, said proximal end being inserted into the body of a patient and said proximal end remaining outside of the body, said distal end being undercut and defining a terminal plane for said body;
at least one blade having a distal and proximal ends, mounted for rotation on said distal end of said body, said distal end of said blade extending beyond said terminal plane of said body during retraction;
a control member mounted for rotation on the distal end of said body and engaging said blade; and
an actuator connected to said control member whereby said blade may be externally manually manipulated to a variety of angular positions for retraction.

9. An endoscopic retractor, comprising:
a body having a longitudinal axis and a distal end and a proximal end, said distal end being inserted into the body of a patient and said proximal end remaining outside of said body, said distal end being undercut and defining a terminal plane for said body;

at least one blade, said blade having a distal end and a proximal end, said proximal end adapted for mounting to said distal end of said body and said distal end of said blade providing retraction; and means by which said blade may be extended from an insertion position in which said blade is substantially parallel to said longitudinal axis of said body, to a second position where said blade is extended beyond said terminal plane of said body during retraction, so as to provide retraction in a direction away from said body, and is at an angle to said longitudinal axis.

10. The retractor of claim 9, including a means for actuating said blade from the proximal end of said body.

11. The retractor of claim 9, comprising of at least two blades, each of said blades being mounted at its proximal end to said body such that said blades may be spaced apart from one another to provide retraction, or aligned with one another for insertion into a patient's body.

12. The retractor of claim 11, wherein said means includes at least one control member for moving said blades.

13. The retractor of claim 11, wherein said means includes at least one actuator for moving said blades from the proximal end of said body.

14. The retractor of claim 11, wherein said means includes means for moving said blades from an insertion position where said blades are closely aligned, to a second retraction position where said distal ends of said blades are spaced apart from one another.

15. An endoscopic retractor adapted to be inserted into the body of a patient through a small surgical port, comprising:

an elongate body having a distal end and a proximal end, said distal end being inserted into the body through said surgical port and said proximal end remaining outside the body, said distal end defining a terminal plane for said body;

at least one blade having distal and proximal ends, said proximal end of said blade being mounted for articulation on said distal end of said body, said distal end of said blade extending proximally beyond said terminal plane of said body during retraction, so as to provide retraction in a direction away from said body with minimal interference from said body and wherein said distal end of said body is undercut to allow said blade to assume a variety of angular positions;

a control member rotatably mounted on said distal end of said body and engaging said proximal end of said blade; and an actuator connected to said control member at said distal end of said body and extending along said body to said proximal end thereof for external manipulation of said blade, said actuator being externally manipulable to cause said control member to articulate about said rotatable mounting, whereby said blade can be variably adjustable to a wide variety of angular positions with respect to the longitudinal axis of said body and achieve retraction in a wide variety of directions.

16. The retractor of claim 15, comprising at least two blades, each of said blades being mounted at the proximal end thereof for articulation on said distal end of said body, such that upon actuation of said control member, said blades are spaced apart from one another.

17. The retractor of claim 16, wherein said blades in their spaced position define an open area between them without obstruction, whereby other surgical procedures may be performed therein.

18. The retractor of claim 16, wherein said blades are mounted such that said blades assume said angular, spaced position simultaneously and proportional to a single movement of said actuator.

19. The retractor of claim 16, wherein said blades are mounted such that their angular and spaced positions result from independent movements of said actuator.

20. The retractor of claim 16, wherein said actuator comprises dual mechanisms, a first mechanism for causing extension of said blades and a second mechanism for causing said blades to be spaced apart.

21. The retractor of claim 16, wherein the retractor comprises a plurality of control members, each of said control members engaging the proximal end of one of said blades, and wherein the retractor comprises a plurality of actuators, each of said actuators being connected to one of said control members, whereby said blades are independently manipulatable.

22. The retractor of claim 21, wherein the number of control members, blades and actuators is the same.

23. The retractor of claim 16, wherein said proximal ends of said blades comprises a lever and said control member engages said lever to manipulate said blades.

24. An endoscopic retractor, comprising:

a body having a distal end and a proximal end, said distal end being inserted into a patient's body and said proximal end remaining outside the patient's body, said distal end defining a terminal plane for said body;

a retracting member having distal and proximal ends, said proximal end of said retracting member being mounted for articulation on said distal end of said body, said distal end of said retracting member extending beyond said terminal plane of said body, said distal end being adapted for retraction of tissues, organs, and the like, and wherein said distal end of said body is undercut to allow said retracting member to assume a wide variety of angular positions; and an actuator connected to said retracting member at said distal end of said body and extending along said body to said proximal end thereof, said actuator being connected to said proximal end of said retracting member and being externally manipulable to cause said retracting member to assume a wide variety of angular positions with respect to the longitudinal axis of said body and achieve retraction in a wide variety of directions.

25. The endoscopic retractor of claim 24, wherein a control member is also mounted for movement in a direction parallel to the longitudinal axis of said body, said longitudinal movement occurring responsive to external manipulation of said actuator, whereby said retracting member may be adjusted to a variety of lateral positions.

26. An endoscopic retractor adapted to be inserted into the body of a patient through an endosurgical port, comprising:

a body having a longitudinal axis and a distal end and a proximal end, said distal end of said body being inserted into the body of a patient and said proximal end of said body remaining outside of said body, said distal end being undercut and defining a terminal plane for said body;

at least two blades, each of said blades having a distal end and a proximal end, said proximal end of said blade being adapted for mounting at said distal end of said body and said distal end of said blade extending beyond said terminal plane of said body;

a first control member mounted at said distal end of said body;

a second control member mounted on said body proximally of said first control member;

a first actuator connected to said first control member whereby movement of said first actuator causes said first control member to engage the proximal ends of said blades, whereby said blades are articulated so as to provide retraction in a wide variety of angular positions with respect to the longitudinal axis of said body; and a second actuator connected to said second control member whereby movement of said second actuator causes said second control member to engage the proximal ends of said blades, whereby said blades are spaced apart from one another.

27. A method of providing retraction in endoscopic surgery, comprising:

creating an opening in the body of a patient;

inserting through said opening a retractor comprising a body having a distal and a proximal end, said distal end being undercut and defining a terminal plane for said body, at least one blade having distal and proximal ends, said distal end extending beyond said terminal plane of said body, and an actuator, such that the distal end of said body is inside the patient and said proximal end remains outside the patient;

positioning said blade to engage a selected internal organ or tissue within the patient's body; and manipulating said actuator, such that said blade assumes any of a wide variety of angular positions with respect to said body, such that said organ or tissue is displaced in any direction by said blade.

28. A method of manipulating organs and tissues during endoscopic surgery, comprising:

creating an opening in the body of a patient;

inserting through said opening a retractor comprising a body having a distal and a proximal end, said distal end being undercut and defining a terminal plane for said body, at least one blade having distal and proximal ends, said distal end extending beyond said terminal plane of said body, and an actuator, such that the distal end of said body is inside the patient and said proximal end remains outside the patient;

manipulating said actuator, such that said blade assumes any of a wide variety of angular positions with respect to said body;

positioning said blade to engage a selected internal organ or tissue within the patient's body; and manipulating said blade such that said distal end of said blade causes said organ or tissue to be dissected.

29. A method of manipulating organs and tissues during endoscopic surgery, comprising:

creating an opening in the body of a patient;

inserting through said opening a retractor comprising a body having a distal and a proximal end, said distal end being undercut and defining a terminal plane for said body, at least two blades each having distal and proximal ends, said distal end extending beyond said terminal plane of said body, and an actuator, such that the distal end of said body is inside the patient and said proximal end remains outside the patient;

manipulating said actuator, such that said blades assume any of a wide variety of angular positions with respect to said body;

positioning said blades such that a selected internal organ or tissue within the patient's body is located between said blades;

manipulating said blades such that said blades grasp said organ or tissue; and exerting a force on said body whereby said organ or tissue grasped between said blades is torn from surrounding tissue.

30. An endoscopic retractor, comprising:

a body having a distal end and a proximal end, said distal end being undercut and defining a terminal plane for said body;

at least one retracting member having distal and proximal ends, said proximal end mounted on said distal end of said body, and said distal end extending beyond the terminal plane of said body;

an actuator connected to said retracting member such that manipulation of said actuator causes said retracting member to assume a wide variety of angular positions with respect to the longitudinal axis of said body and achieve retraction in a wide variety of directions.

* * * * *